(12) United States Patent
Han (10) Patent No.: US 12,357,277 B2
(45) Date of Patent: Jul. 15, 2025

(54) ULTRASOUND IMAGING SYSTEM AND METHOD FOR SELECTING AN ANGULAR RANGE FOR FLOW-MODE IMAGES

(71) Applicant: GE Precision Healthcare LLC, Wauwatosa, WI (US)

(72) Inventor: JiHye Han, Seongnam-si (KR)

(73) Assignee: GE Precision Healthcare LLC, Wauwatosa, WI (US)

( * ) Notice: Subject to any disclaimer, the term of this patent is extended or adjusted under 35 U.S.C. 154(b) by 37 days.

(21) Appl. No.: 17/534,124

(22) Filed: Nov. 23, 2021

(65) Prior Publication Data

US 2023/0157669 A1    May 25, 2023

(51) Int. Cl.
| | |
|---|---|
| *A61B 8/00* | (2006.01) |
| *A61B 8/06* | (2006.01) |
| *G06F 3/0338* | (2013.01) |
| *G06F 3/0354* | (2013.01) |
| *G06F 3/0362* | (2013.01) |

(52) U.S. Cl.
CPC ................ *A61B 8/469* (2013.01); *A61B 8/06* (2013.01); *A61B 8/461* (2013.01); *G06F 3/0338* (2013.01); *G06F 3/03547* (2013.01); *G06F 3/0362* (2013.01)

(58) Field of Classification Search
CPC ........... A61B 8/469; A61B 8/06; A61B 8/461; G06F 3/0338; G06F 3/03547; G06F 3/0362
See application file for complete search history.

(56) References Cited

U.S. PATENT DOCUMENTS

| | | | |
|---|---|---|---|
| 2007/0171196 A1* | 7/2007 | Pfingsten | G06F 3/0488 |
| | | | 345/156 |
| 2013/0235000 A1* | 9/2013 | Lee | F24C 7/082 |
| | | | 345/184 |
| 2014/0371594 A1 | 12/2014 | Flynn | |
| 2016/0074010 A1* | 3/2016 | Kierulf | A61B 8/469 |
| | | | 600/447 |
| 2019/0015078 A1* | 1/2019 | Saad | A61B 8/488 |
| 2019/0216430 A1 | 7/2019 | Hoctor | |
| 2021/0145399 A1* | 5/2021 | Xie | A61B 8/5246 |

* cited by examiner

*Primary Examiner* — Joel Lamprecht
(74) *Attorney, Agent, or Firm* — Bookoff McAndrews, PLLC (57) ABSTRACT

An ultrasound imaging system and method for flow-mode imaging. A method of ultrasound imaging includes displaying an initial ultrasound image, receiving a selection of a flow region through a user interface, and receiving a selection of an angular range through the user interface. The method includes displaying a flow-mode image on the display device after receiving both the selection of the flow region and the selection of the angular range, wherein the flow-mode image represents flow information that is both within the flow region and within the selected angular range. Wherein the flow-mode image does not represent flow information that is either outside of the flow region or outside of the angular range.

18 Claims, 11 Drawing Sheets

ULTRASOUND IMAGING SYSTEM AND METHOD FOR SELECTING AN ANGULAR RANGE FOR FLOW-MODE IMAGES

FIELD OF THE INVENTION

This disclosure relates generally to an ultrasound imaging system and method for setting an angular range for use with flow-mode images.

BACKGROUND OF THE INVENTION

Using various conventional ultrasound modes, such as color flow and vector flow, it is possible to determine velocities for various flowing fluids, such as blood. For example, while in a color flow imaging mode, Doppler information is color-encoded and the colors are overlaid on a grey-scale (B-mode) image. While in a vector-flow imaging mode, the direction information of the fluid is represented using depictions of lines or vectors that are overlaid on a grey-scale (B-mode) image.

Using flow-mode imaging, such as color flow or vector flow imaging, provides the clinician with valuable information about the way the fluid is moving. However, since conventional flow-mode imaging typically represents velocity information of fluid moving in many different directions, it is oftentimes difficult for the clinician to use the flow-mode imaging to accurately assess a patient and/or diagnose a specific condition. For example, it may be difficult for the clinician to easily identify the relevant portions of the flow-mode images due to the presence of velocity information from many different directions when velocity information from only a subset of the directions is needed to make an assessment or diagnosis.

Therefore, for these and other reasons, an improved ultrasound imaging system and method of adjusting an angular range for use with the display of a flow-mode image is desired.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes displaying an initial ultrasound image, and receiving, through a user interface, a selection of a flow region, wherein the flow region includes a subset of the initial ultrasound image. The method includes receiving, through the user interface, a selection of an angular range, wherein the angular range is less than 360 degrees. The method includes displaying a flow-mode image on the display device after receiving both the selection of the flow region and the selection of the angular range, wherein the flow-mode image represents flow information that is both within the flow region and within the selected angular range, and wherein the flow-mode image does not represent flow information that is either outside the flow region or outside of the angular range.

In another embodiment, an ultrasound imaging system includes a user interface, an ultrasound probe, a display device, and a processor. The processor is configured to display an initial ultrasound image on the display device. The processor is configured to receive a selection of a flow region via the user interface, wherein the flow region includes a subset of the initial ultrasound image. The processor is configured to receive a selection of an angular range via the user interface, wherein the angular range is less than 360 degrees. The processor is configured to display a flow-mode image on the display device, wherein the flow-mode image represents flow information that is both within the flow region and within the selected angular range. Wherein the flow-mode image does not represent flow information that is either outside the flow region or outside the angular range.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized, and that logical, mechanical, electrical, and other changes may be made without departing from the scope of the embodiments. The following detailed description is, therefore, not to be taken as limiting the scope of the invention.

Figure 1:
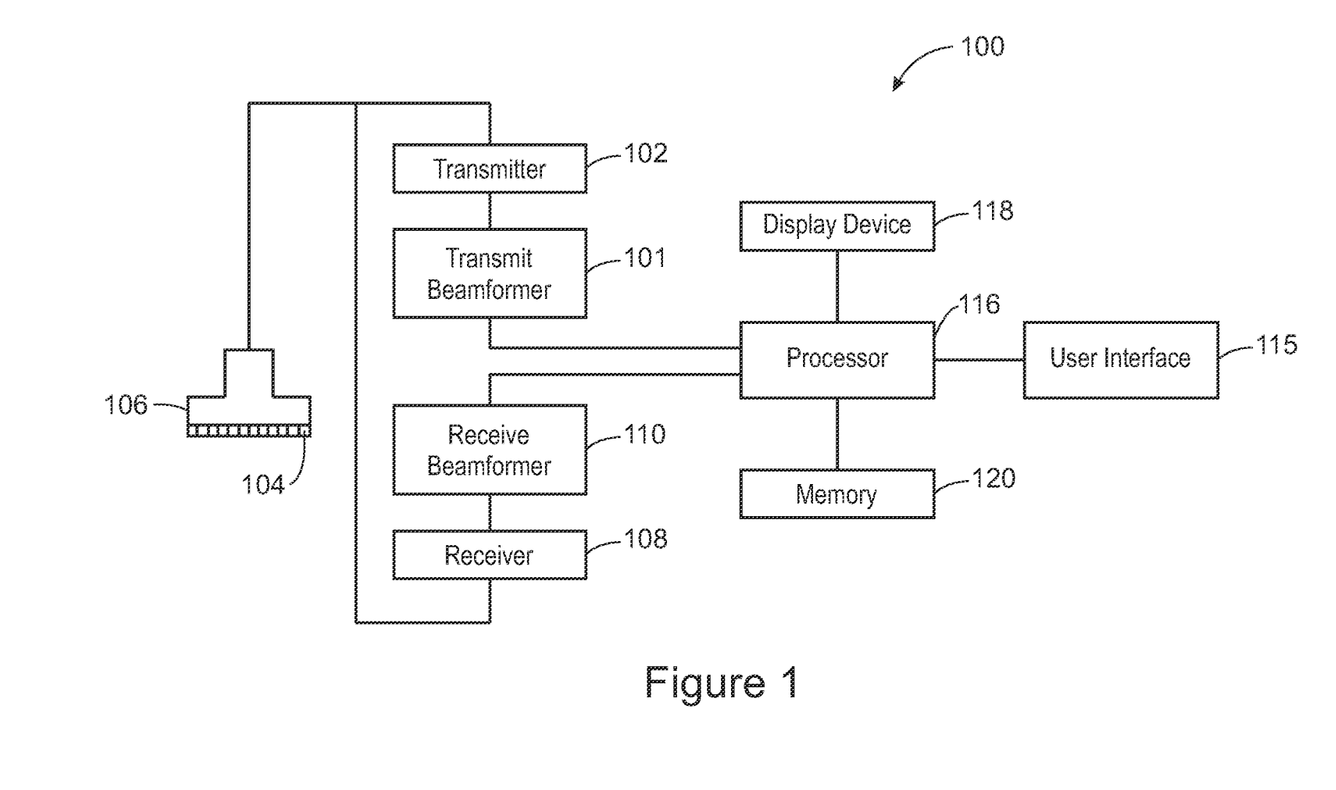
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within an ultrasound probe 106 to emit pulsed ultrasonic signals into a body (not shown) through one or more transmit events. The ultrasound probe 106 may be any type of ultrasound probe. For example, the ultrasound probe 106 may be a linear array probe, a curved-linear array probe, a convex array probe, a phased array probe, a 2D matrix array probe capable of 3D or 4D scanning, a mechanical 3D probe, etc. Still referring to FIG. 1, the pulsed ultrasonic signals are back-scattered from structures in the body to produce echoes that return to the elements 104. The ultrasound probe 106 may be in electrical communication with one or more other components of the ultrasound imaging system 100 via wired and/or wireless techniques. The echoes are converted into electrical signals by the elements 104 and the electrical signals are received by a receiver 108. The electrical signals representing the received echoes are passed through a receive beamformer 110 that outputs ultrasound data. According to some embodiments, the ultrasound probe 106 may contain electronic circuitry to do all or part of the transmit beamforming and/or the receive beamforming. For example, all or part of the transmit beamformer 101, the transmitter 102, the receiver 108 and the receive beamformer 110 may be situated within the ultrasound probe 106. According to some embodiments, the ultrasound probe 106 may be configured to wirelessly communicate with a phone-sized or tablet-sized device and the ultrasound probe 106 and either the phone-sized device or the tablet-sized device may collectively perform all the functions associated with the elements identified on FIG. 1. The terms "scan" or "scanning" may also be used in this disclosure to refer to acquiring data through the process of transmitting and receiving ultrasonic signals. The terms "data" and "ultrasound data" may be used in this disclosure to refer to either one or more datasets acquired with an ultrasound imaging system 100. A user interface 115 may be used to control operation of the ultrasound imaging system 100. The user interface 115 may be used to control the input of patient data, or to select various modes, operations, parameters, and the like. The user interface 115 may include one or more user input devices such as a keyboard, hard keys, a touch pad, a track ball, rotary controls, sliders, soft keys, or any other user input devices. According to some embodiments, the user interface 115 may include a touch panel that is part of a touchscreen. An exemplary touchscreen will be described hereinafter with respect to FIG. 2.

The ultrasound imaging system 100 includes a display device 118. The display device 118 may include any type of display screen or display that is configured to display images, text, graphical user interface elements, etc. The display device 118 may be, for example, a cathode ray tube (CRT) display, a light-emitting diode (LED) display, an organic light-emitting diode (OLED) display, a liquid crystal display (LCD), etc. According to some embodiments, the display device 118 may be a display screen that is a component of a touchscreen.

Figure 2:
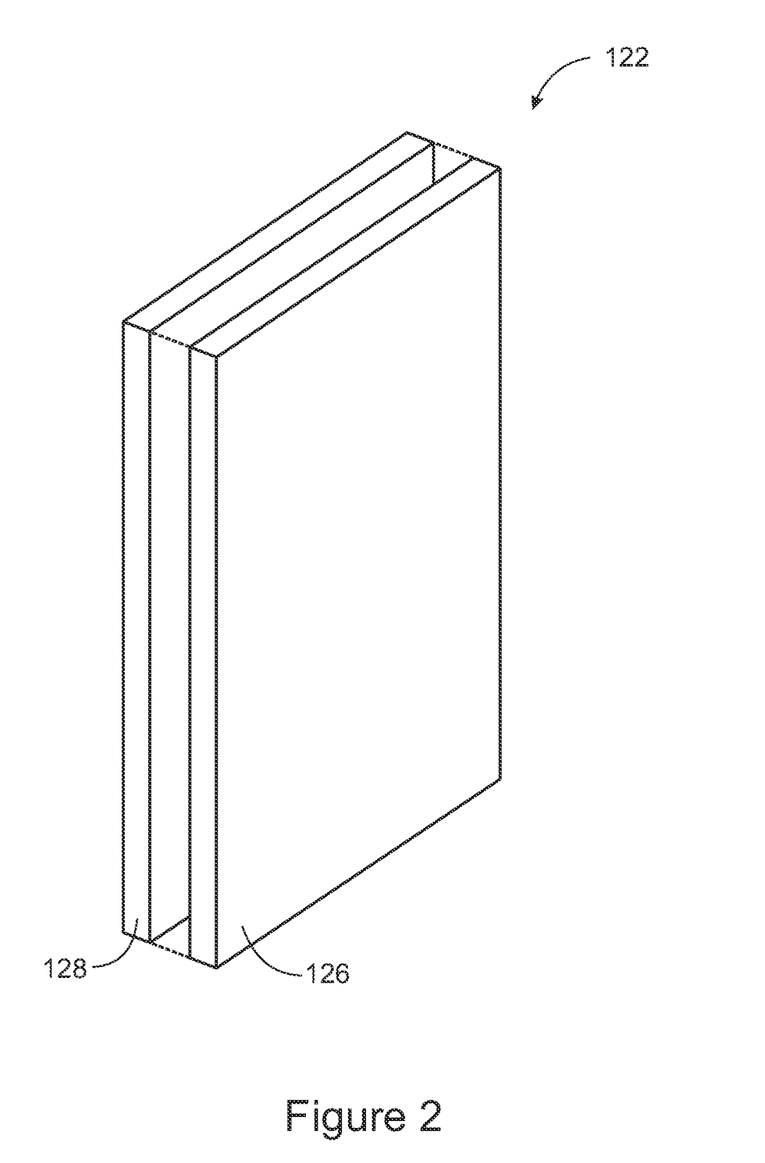
FIG. 2 is an exploded representation of touchscreen in accordance with an embodiment.

As discussed above, the display device 118 and the user interface 115 may be components in a touchscreen. FIG. 2 is an exploded representation of a touchscreen 122 in accordance with an exemplary embodiment. The touchscreen 122 includes a touch panel 126 and a display screen 128 in accordance with an embodiment. The touch panel 126 may be located behind the display screen 128 or in front of the display screen 128 according to various non-limiting examples. For embodiments where the touch panel 126 is positioned in front of the display screen 128, the touch panel 126 may be configured to be substantially transparent so that the user may see images displayed on the display screen 128. The touch panel 126 may utilize any type of technology configured to detect a touch or gesture applied to the touch panel 126 of the touchscreen 122. As discussed hereinabove, the display device 118 may include a display screen of a touchscreen such as the display screen 128, and the user interface 115 may include a touch panel, such as the touch panel 126 of the touchscreen 122. The touch panel 126 may be configured to detect single-point touch inputs and/or multi-point touch inputs according to various embodiments. The touch panel 126 may utilize any type of technology configured to detect a touch or gesture applied to the touch panel 126 of the touchscreen 122. For instance, the touch panel 126 may include resistive sensors, capacitive sensors, infrared sensors, surface acoustic wave sensors, electromagnetic sensors, near-filed imaging sensor, or the like. Some embodiments may utilize the touch panel 126 of the touchscreen 122 to provide all of the user interface functionalities for the ultrasound imaging system 100, while other embodiments may also utilize one or more other components as part of the user interface 115.

Referring back to FIG. 1, the ultrasound imaging system 100 also includes a processor 116 to control the transmit beamformer 101, the transmitter 102, the receiver 108 and the receive beamformer 110. The user interface 115 is in electronic communication with the processor 116. The processor 116 may include one or more central processing units (CPUs), one or more microprocessors, one or more microcontrollers, one or more graphics processing units (GPUs), one or more digital signal processors (DSP), and the like. According to some embodiments, the processor 116 may include one or more GPUs, where some or all of the one or more GPUs include a tensor processing unit (TPU). According to embodiments, the processor 116 may include a field-programmable gate array (FPGA), or any other type of hardware capable of carrying out processing functions. The processor 116 may be an integrated component or it may be distributed across various locations. For example, according to an embodiment, processing functions associated with the processor 116 may be split between two or more processors based on the type of operation. For example, embodiments may include a first processor configured to perform a first set of operations and a second, separate processor to perform a second set of operations. According to embodiments, one of the first processor and the second processor may be configured to implement a neural network. The processor 116 may be configured to execute instructions accessed from a memory. According to an embodiment, the processor 116 may be in electronic communication with the ultrasound probe 106, the receiver 108, the receive beamformer 110, the transmit beamformer 101, and the transmitter 102. For purposes of this disclosure, the term "electronic communication" may be defined to include both wired and wireless connections. The processor 116 may control the ultrasound probe 106 to acquire ultrasound data. The processor 116 controls which of the elements 104 are active and the shape of a beam emitted from the ultrasound probe 106. The processor 116 is also in electronic communication with a display device 118, and the processor 116 may process the ultrasound data into images for display on the display device 118. According to embodiments, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. The processor 116 may be configured to scan-convert the ultrasound data acquired with the ultrasound probe 106 so it may be displayed on the display device 118. Displaying ultrasound data in real-time may involve displaying the ultrasound data without any intentional delay. For example, the processor 116 may display each updated image frame as soon as each updated image frame of ultrasound data has been acquired and processed for display during the display of a real-time image. Real-time frame rates may vary based on the size of the region or volume from which data is acquired and the specific parameters used during the acquisition. According to other embodiments, the data may be stored temporarily in a buffer (not shown) during a scanning session and processed in less than real-time. According to embodiments that include a software beamformer, the functions associated with the transmit beamformer 101 and/or the receive beamformer 110 may be performed by the processor 116.

According to an embodiment, the ultrasound imaging system 100 may continuously acquire ultrasound data at a frame-rate of, for example, 10 Hz to 30 Hz. Images generated from the data may be refreshed at a similar frame-rate. Other embodiments may acquire and display data at different rates. For example, some embodiments may acquire ultrasound data at a frame rate of less than 10 Hz or greater than 30 Hz depending the size of each frame of data and the parameters associated with the specific application. For example, many applications involve acquiring ultrasound data at a frame rate of about 50 Hz. A memory 120 is included for storing processed frames of acquired data. In an exemplary embodiment, the memory 120 is of sufficient capacity to store frames of ultrasound data acquired over a period of time at least several seconds in length. The frames of data are stored in a manner to facilitate retrieval thereof according to its order or time of acquisition. The memory 120 may comprise any known data storage medium.

In various embodiments of the present invention, data may be processed by other or different mode-related modules by the processor 116 (e.g., B-mode, M-mode, color M-mode, spectral Doppler, Elastography, TVI, strain, strain rate, color flow, vector flow, and the like) to form 2D or 3D data. For example, one or more modules may generate B-mode, M-mode, color M-mode, spectral Doppler, Elastography, TVI, strain, strain rate, color flow, vector flow, and the like. The data may be processed to generate a flow-mode image. A flow-mode image is an ultrasound image that is used to present information about a moving or flowing fluid. The flow-mode image may, for instance present velocity information about a flowing fluid. Non-limiting examples of flow-mode images include color flow images and vector flow images. A color flow image may be generated while in a color flow imaging mode and a vector flow image may be generated while in a vector flow imaging mode. While color flow images and vector flow images were presented as two examples of flow-mode images, it should be appreciated by those skilled in the art that other types of flow-mode images may be used to show flow information according to various embodiments. The image beams and/or frames are stored, and timing information indicating a time at which the data was acquired in memory may be recorded. The modules may include, for example, a scan conversion module to perform scan conversion operations to convert the image frames from beam space coordinates to display space coordinates. A video processor module may be provided that reads the image frames from a memory, such as the memory 120, and displays the image frames in real time while a procedure is being carried out on a patient. The video processor module may store the image frames in an image memory, from which the images are read and displayed.

Figure 3:
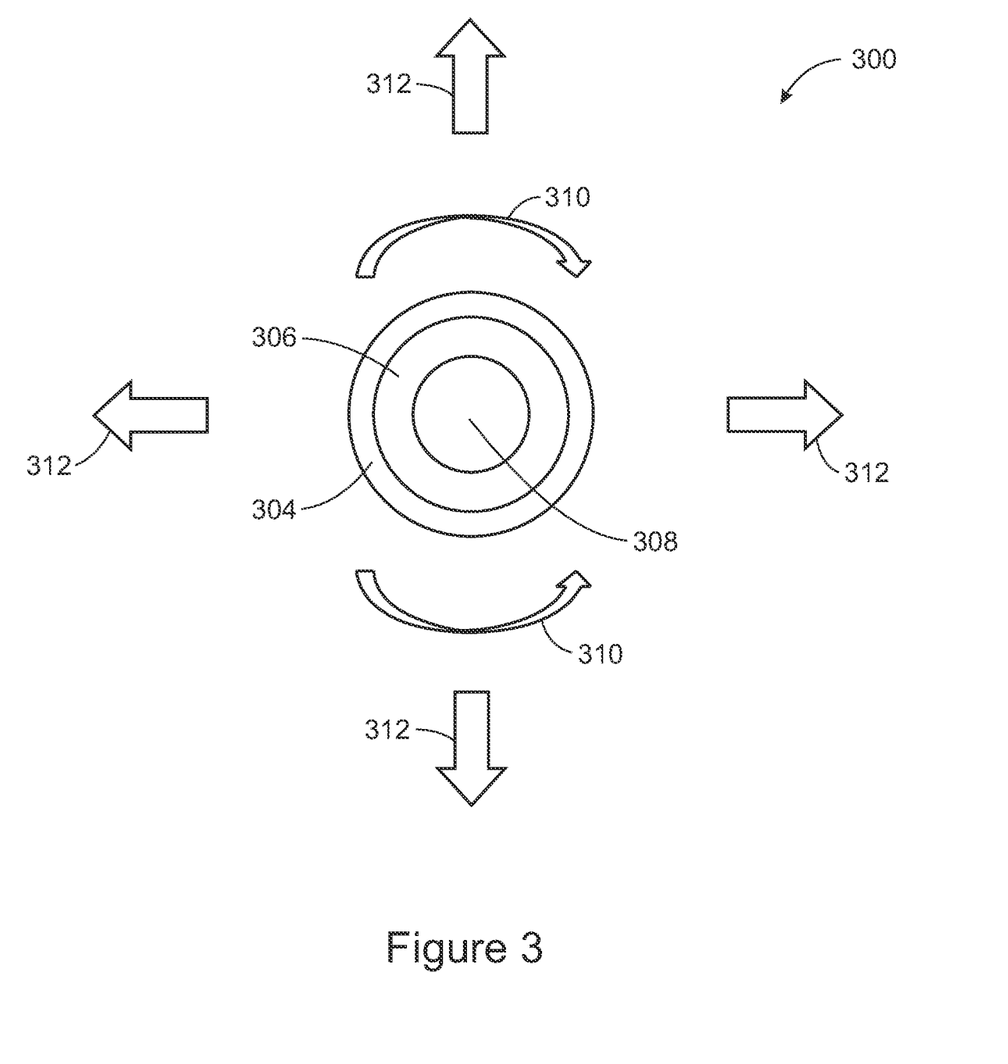
FIG. 3 is a top view of a multi-function controller in accordance with an embodiment.
Figure 4:
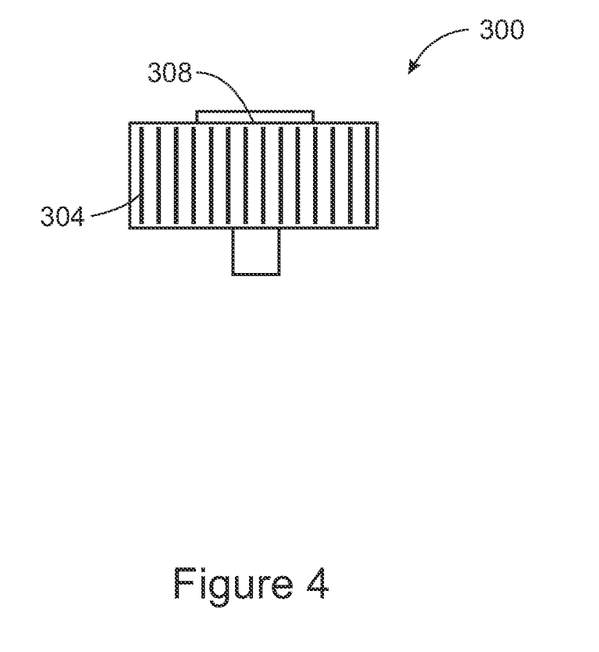
FIG. 4 is a side view of a multi-function controller in accordance with an embodiment.

According to some embodiments, the user interface 115 may include a multi-function controller. The multi-function controller is configured to accept inputs or commands by either tilting the multi-function controller like a joystick (i.e., "joystick inputs") or by rotating some or all of the multi-function controller like a rotary or dial. The multi-function controller is therefore able to receive both rotational inputs and joystick inputs. FIG. 3 is a top view of a multi-function controller 300 in accordance with an embodiment. FIG. 4 is a side view of the multi-function controller 300 in accordance with an embodiment. The multi-function controller 300 is configured to receive commands through a variety of different physical inputs. For example, the multi-function controller 300 is configured to be tilted like a joystick. The multifunction controller 300 may, for instance, be tiled about a pivot point. The multi-function controller 300 is configured to be tilted in any direction as indicted by arrows 312. The multifunction controller 300 is also configured to receive rotational inputs. The multi-function controller 300 may be configured to receive a command input selecting the angular range. For example, the multi-function controller 300 includes an outer bezel 304 that is configured to be rotated about an inner bezel 306. The clinician may rotate the outer bezel 304 with respect to the inner bezel 306 as indicated by curved arrows 310. According to other embodiments, the multi-function controller may not include a separate rotatable bezel. Instead, the multi-function controller may be configured as a joystick that is rotatable about a longitudinal axis. (not shown) The multi-function controller 300 shown in FIG. 3 also includes a button 308. Other embodiments may not include the button 308, but may instead be configured to receive a press input by depressing the multi-function controller 300 in a direction parallel to a longitudinal axis. The clinician may input a button press command via the button 308. The multi-function controller 300 is configured to receive physical commands through three different types of physical inputs: tilting, rotating, and pressing. According to other embodiments, the multi-function controller may not include the button 308.

Figure 5:
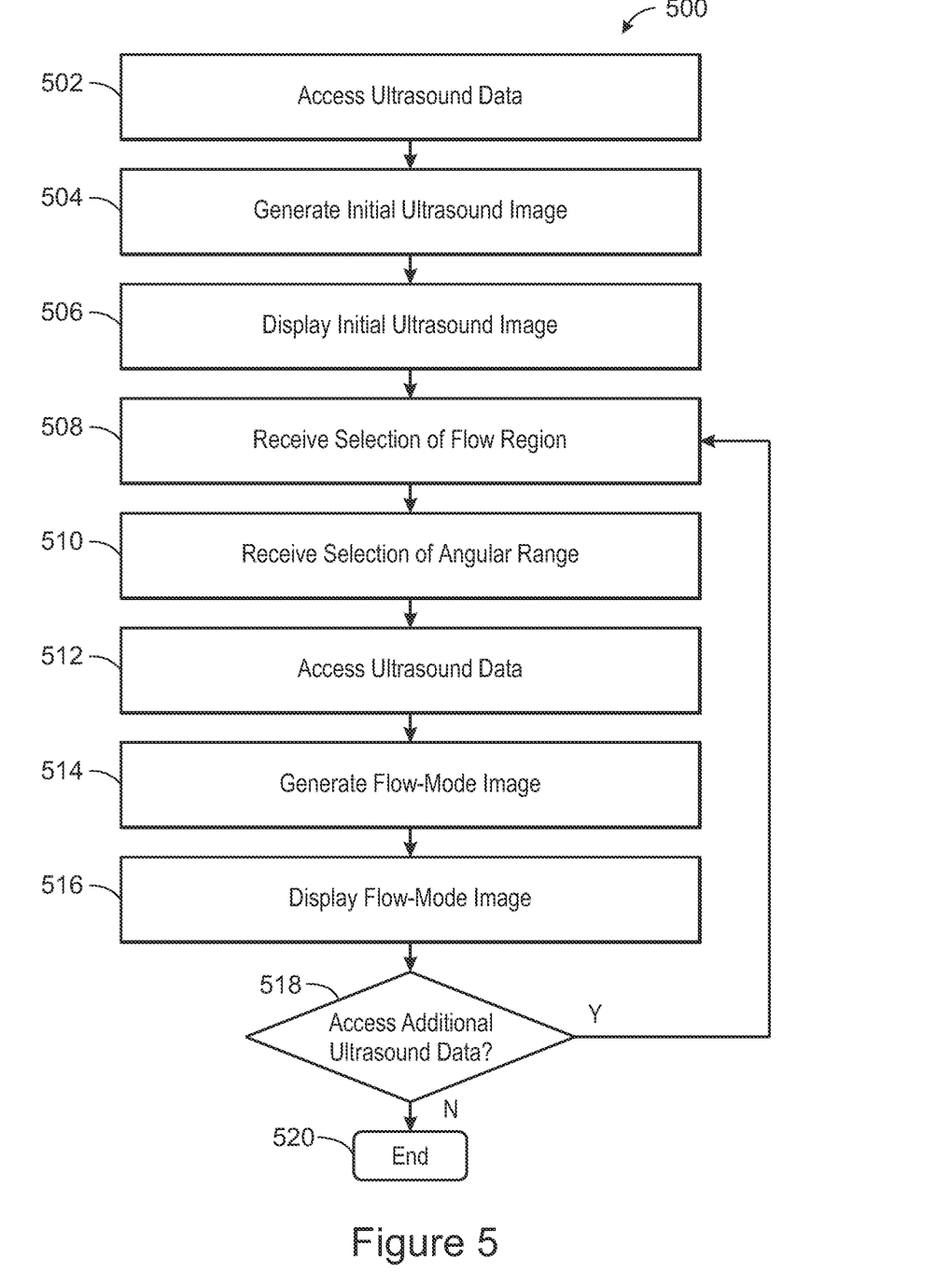
FIG. 5 is a flow chart of a method in accordance with an embodiment.

FIG. 5 illustrates a flowchart of an embodiment of a method 500. The method 500 shown in FIG. 5 may be performed with the ultrasound imaging system 100 shown in FIG. 1 according to an exemplary embodiment. The technical effect of the method 300 is the display of a flow-mode image representing flow information of a selected flow region within a selected angular range.

At step 502, the processor 116 accesses ultrasound data. The ultrasound data accessed by the processor 116 at step 502 may be accessed in real-time as the ultrasound data is acquired, or the ultrasound data accessed at step 512 may be retrieved from memory based an acquisition performed at an earlier time. According to an embodiment, the processor 116 may access the ultrasound data from a memory, such as the memory 120. According to other embodiments, the processor 116 may access the ultrasound data from a remote memory or server. The ultrasound data may be accessed in real-time during a live ultrasound procedure or retrospectively after the ultrasound examination has been completed. For example, the processor 116 may access the ultrasound data from an ultrasound examination that was performed earlier on the same day as the method 500. Or the processor 116 may access the ultrasound data from an ultrasound examination performed days before the implementation of the method 500. According to various embodiments, the processor 116 may access the ultrasound data directly from other components, such as the receive beamformer 110.

At step 504, the processor 116 generates an initial ultrasound image. The initial ultrasound image may be generated while in any ultrasound image mode. For example, the initial image may be a B-mode image, a flow-mode image, such as a color flow image, a vector flow image, or any other type of ultrasound image.

Figure 6:
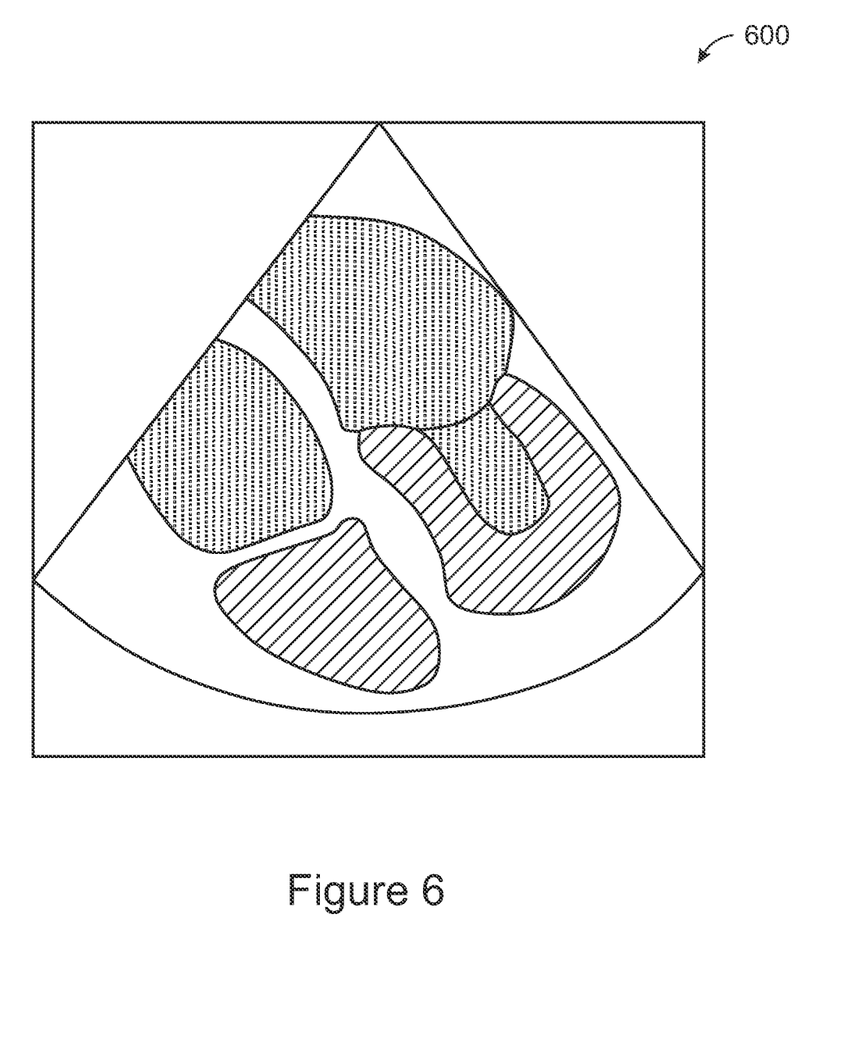
FIG. 6 is a representation of an ultrasound image in accordance with an embodiment.

FIG. 6 is an initial ultrasound image 600 in accordance with an embodiment. The initial ultrasound image 600 shown in FIG. 6 is a color flow image, but, as discussed hereinabove, the initial ultrasound image in other embodiments may be any type of ultrasound image mode. For example, the initial ultrasound image may be a B-mode image according to various embodiments.

The initial ultrasound image 600 shown in FIG. 6 is a color flow image. Color flow images typically use color to represent the direction of flow. In conventional color flow images, flow in a direction towards the transducer is represented in red and flow in a direction away from the transducer is represented in blue. In FIG. 6, red areas are represented with diagonal hatching and blue areas are represented with stippling. As discussed hereinabove, a color flow image is an example of a flow-mode image. As such, the initial ultrasound image 600 shown in FIG. 6 is a flow-mode image. However, the initial ultrasound image may not be a flow-mode image according to other embodiments. For example, the initial ultrasound image 600 may be a B-mode image according to various embodiments.

At step 506, the initial ultrasound image, such as the initial ultrasound image 600, is displayed on the display device 118. According to some embodiments, the initial ultrasound image may be based on the most recently acquired frame of ultrasound data during a live or real-time ultrasound acquisition.

At step 508, the processor 116 receives a selection of a flow region via the user interface 115. The flow region represents a subset of the initial ultrasound image. The selection of the flow region will be described in detail hereinafter.

The clinician may interact with the user interface 115 to select the flow region that is received by the processor 116 at step 508. The clinician may interface with the user interface 115 in any number of ways to select the flow region. A non-limiting list of ways that the clinician may interact with the user interface 115 to select the flow region includes: designating a boundary around the flow region, highlighting the flow region, positioning a ROI (region of interest) around the flow region, or positioning an origin on the initial image 600 to define the flow region.

According to an embodiment, the clinician may select the flow region by designating a boundary around the flow region. The clinician may, for example, drawn or trace an outline or boundary around the flow region on the initial ultrasound image using inputs to a mouse, a trackball, a touchpad, or a touch panel of touchscreen to designate the boundary. According to embodiments where the clinician designates the boundary on a touchscreen, the clinician may simply input a gesture or gestures tracing the boundary of the desired flow region on the initial ultrasound image. According to embodiments where the clinician designates the flow region using a mouse, trackball, or touchpad, the clinician may move a cursor or pointer on the initial ultrasound image to designate the flow region.

At step 510, the processor 116 receives a selection of an angular range from the user interface 115. The angular range determines the directional range of flow information displayed in the flow region. For example, according to an embodiment, the processor 116 will only display flow information that is flowing in a direction within the selected angular range.

For instance, the clinician may provide one or more user inputs through the user interface 115. For example, the clinician may select the angular range using one or more of numbers on a keyboard or keypad, one or more gestures entered through a touchscreen or touchpad; or using a touchscreen, touchpad, mouse, or trackball to interface with a graphical user interface displayed on the display 118. The clinician may provide the selection of the angular range via a multi-function controller, such as the multi-function controller 300.

According to an exemplary embodiment, the clinician may input a selection of the angular range using the multi-function controller 300. The clinician may rotate the multi-function controller 300 to designate the angular range. For example, the clinician may rotate the outer bezel 304 of the multi-function controller 300 to a first rotational position and press a button (i.e., a first button press input), such as the button 308. The press of the button 308 may establish a first limit of the angular range. The user may then rotate the outer bezel 304 to a second rotational position and press the button 308 (i.e., a second button press input) to establish a second limit of the angular range. The angular range may be defined as the range of angles between the first limit of the angular range and the second limit of the angular range. According to various embodiments the button pressed to designate the first limit of the angular range and the second limit of the angular range may be located on a part of the user interface 115 other than the multi-function controller 300.

After the processor 116 has received the selection of the flow region at step 508 and the selection of the angular range at step 510, the method 500 advances to step 512 where the processor 116 accesses ultrasound data. The ultrasound data may be accessed in real-time during a live ultrasound procedure or the ultrasound data may be accessed retrospectively after the ultrasound examination has been completed. The ultrasound data accessed at step 512 may be either the same ultrasound data that was accessed at step 502, or the ultrasound data accessed at step 512 may be different than the ultrasound data that was accessed at step 502. The processor 116 may access the ultrasound data at step 512 from a memory such as the memory 120. According to other embodiments, the processor 116 may access the ultrasound data from a remote memory or server. According to various embodiments, the processor 116 may access the ultrasound data directly from other components, such as the receive beamformer 110. The ultrasound data accessed by the processor 116 at step 512 may be accessed in real-time as the ultrasound data is acquired, or the ultrasound data accessed at step 512 may be retrieved from memory based an acquisition performed at an earlier time.

As ultrasound is oftentimes used as a real-time imaging modality, it is anticipated that in many embodiments the method 500 will be implemented in real-time while ultrasound data is being acquired during an ultrasound examination. During embodiments where the data is acquired in real-time, it is anticipated that the ultrasound data accessed at step 512 will have been acquired more recently than the ultrasound data accessed at step 502. For example, the ultrasound data accessed at step 502 may have been acquired at an earlier point in time during the ultrasound examination than the ultrasound data accessed at step 512.

At step 514, the processor 116 generates a flow-mode image based on the ultrasound data accessed at step 512. The flow-mode image represents flow information that is both within the flow region (selected during step 508) and within the angular range (selected during step 510), and wherein the flow-mode image does not represent flow information that is either outside the flow region or outside of the angular range.

Based on the selection of the flow region (received at step 508) and the selection of the angular range (received at step 510), the processor 116 is able to generate and display a flow-mode image that shows only the flow information that is desired to be seen by the clinician. For example, the clinician may select the flow region to include only a subset of the anatomical regions displayed in the initial ultrasound image. This allows the clinician to view only the organs or structures that are specifically of interest for the current ultrasound examination. Additionally, the method 500 only presents flow information within the angular range selected at step 510. The clinician is therefore able to use the angular range like a filter to limit the total amount of flow information displayed in the flow-mode image at step 516. For example, the clinician may select the first limit of the angular range and the second limit of the angular range so that the angular range only includes the flow directions that are specifically of interest for a particular ultrasound examination or study. By displaying only the flow information from within the angular range, the method 500 presents a flow-mode image that includes only the flow information that the clinician requested.

If it is desired to access additional ultrasound data at step 518, the method 500 returns to step 508. Steps 508, 510, 512, 514, 516, and 518 may be iteratively repeated multiple times as long as it is desired to access additional ultrasound data at step 518. If it is not desired to access additional ultrasound data at step 518, the method 500 advances to step 520, wherein the method 500 ends.

According to an embodiment, the method 500 may iteratively repeat steps 508, 510, 512, 514, 516, and 518 during a real-time or live ultrasound acquisition. For example, the processor 116 may generate and display an updated flow-mode image during each iteration of steps 508, 510, 512, 514, 516, and 518. If the clinician does not enter an updated selection of the flow region at step 508, the processor 116 may use the selection of the flow region from the previous iteration of steps 508, 510, 512, 514, 516, and 518. Likewise, if the clinician does not enter an updated selection of the angular range at step 510, the processor 116 may use the selection of the flow region from the previous iteration of steps 508, 510, 512, 514, 516, and 518. However, if the clinician enters an updated selection of the flow region and/or an updated selection of the angular range at steps 508 and 510 respectively, the processor 116 will use the updated flow region 508 and/or the updated angular range when generating and displaying the flow mode image during that iteration of steps 514 and 516.

The method 500 provides an easy way for the clinician to select the flow region and the angular range for a flow-mode image. As discussed hereinabove, the selection of the flow region and/or the selection of the angular range may be used as filters to allow the clinician to only see specific flow information in the flow-mode image. The method 500 allows the clinician to adjust the selection of flow region and/or the angular range while multiple iterations of steps 508, 510, 512, 514, 516, and 518 are being performed. This allows the clinician greater flexibility and enhances the ease with which the clinician is able to make a diagnosis or assessment based on the flow-mode image.

For example, the clinician may fine-tune the size and position of the flow region in order to result in a flow-mode image that only shows the desired anatomy. Additionally, the clinician may adjust the angular range of the flow information displayed in the flow-mode image. As described previously, the clinician may adjust the angular range while in the process of a real-time ultrasound acquisition. The clinician may make a change in one or both of the selection of the flow region and/or the selection of the angular range and quickly see the result of the change in the flow-mode image generated and displayed after the change. The clinician may, for instance, quickly and easily view flow information in the flow-mode image from different angular ranges until the clinician identifies the angular range that would be the most helpful for the current diagnosis or evaluation. Since it is possible to be acquiring additional frames of ultrasound data in real-time while the method 500 is being performed, it is possible to display flow-mode images reflecting the changes in the selection of the flow region and/or the selection of the angular range in real-time or in near real-time.

Figure 7:
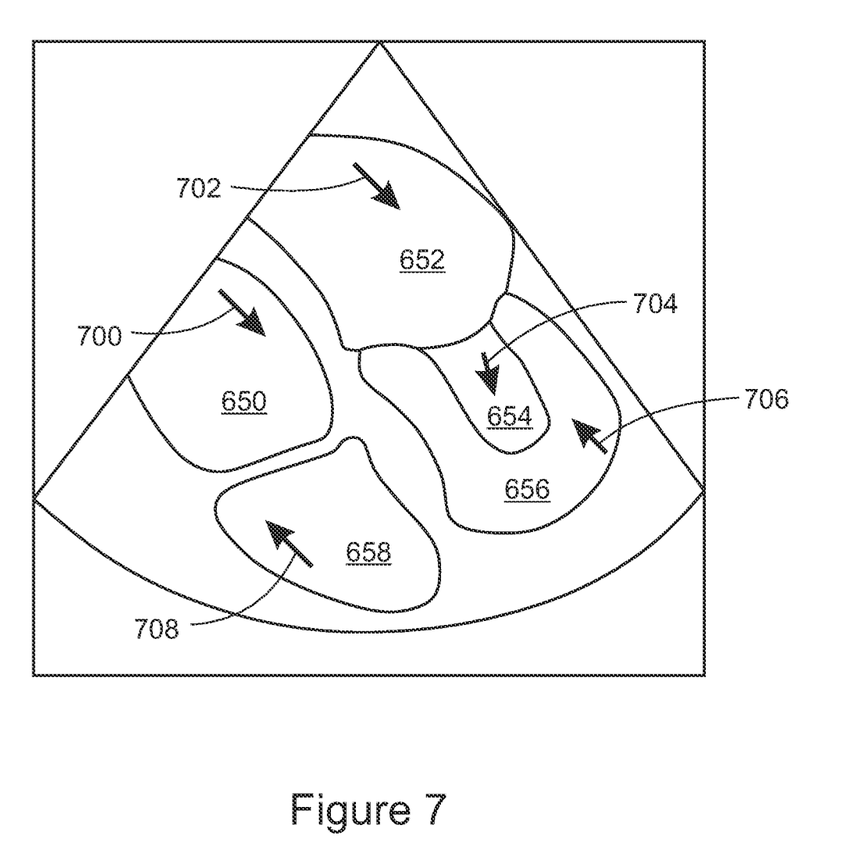
FIG. 7 is a schematic representation of an ultrasound image in accordance with an embodiment.

FIG. 7 is a schematic representation of the flow information that is represented by the initial ultrasound image 600 (FIG. 6), which is a color flow image in accordance with an embodiment. FIG. 7 represents the same anatomy that is shown in the initial ultrasound image 600. FIG. 7 includes 5 separate regions that are depicted in the initial ultrasound image 600. FIG. 7 includes a first region 650, a second region 652, a third region 654, a fourth region 656, and a fifth region 658. Within each of the regions, the direction of flow is generally the same. FIG. 7 includes an arrow in each of the regions. The arrow represents the direction of flow in the respective region. For example, the first region 650 includes a first arrow 700; the second region 652 includes a second arrow 702; the third region 654 includes a third arrow 704; the fourth region 656 includes a fourth arrow 706; and the fifth region 658 includes a fifth arrow 708. The first arrow 700 and the second arrow 702 are both pointed at 145 degrees. This means that the direction of flow in the first region 658 is the same as the direction of flow in the second region 652. The fourth arrow 656 and the fifth arrow 658 are both pointed at 330 degrees. This means that the direction of flow in the fourth region 656 is the same as the direction in the fifth region 658. The third arrow 704 is pointed at 170 degrees. FIG. 7 will be used to help explain FIGS. 8, 9, 10, and 11.

Figure 8:
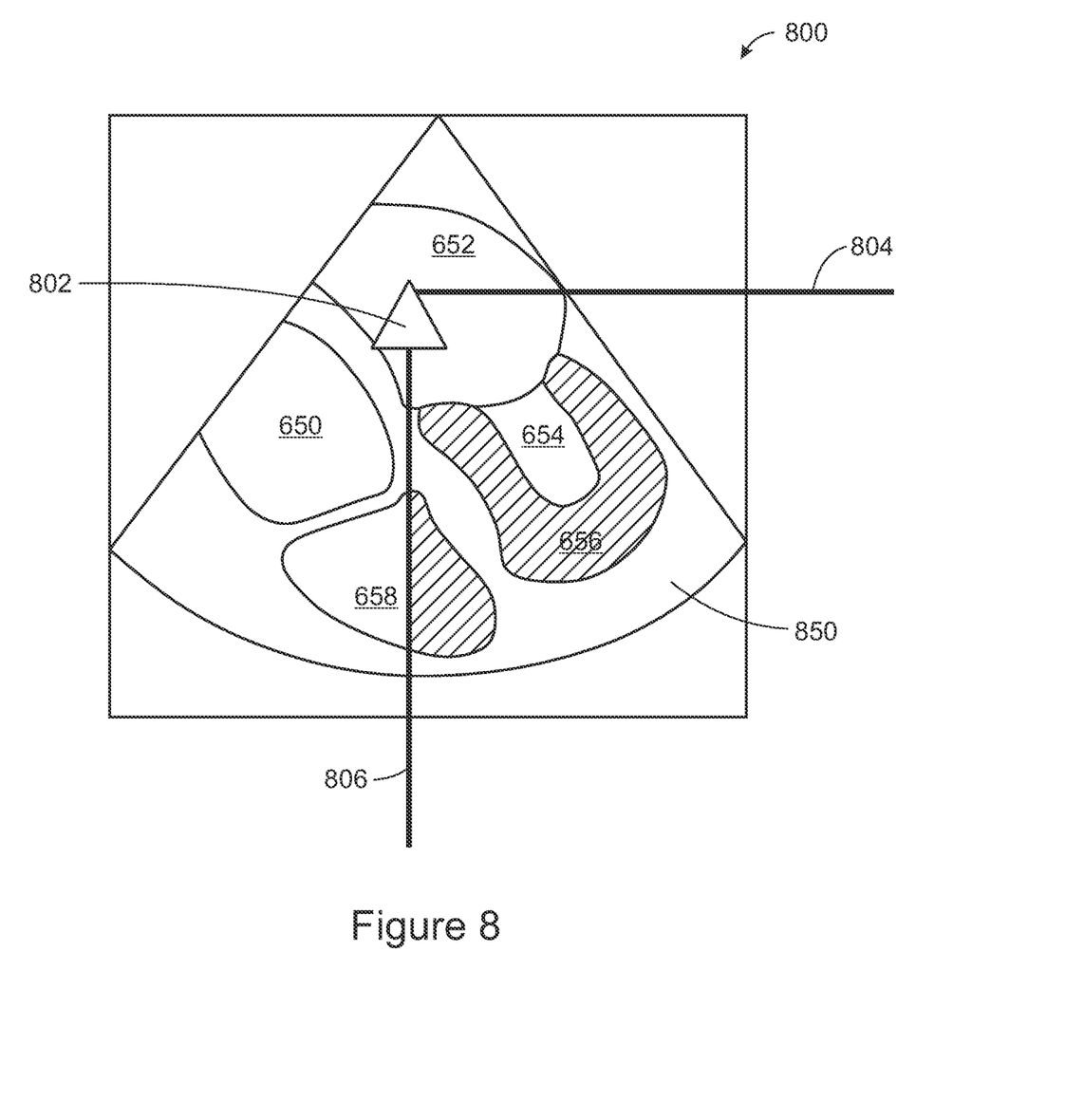
FIG. 8 is a representation of a flow-mode image in accordance with an embodiment.

FIG. 8 is a representative of a flow-mode image 800 in accordance with an embodiment. The flow-mode image 800 is generated using the same underlying flow information as that shown in FIGS. 6 and 7 in accordance with an embodiment. However, FIG. 8 is generated after the selection of a flow region and the selection of an angular range. In FIG. 6, flow information for the entire image is represented from an angular range of 0 degrees to 360 degrees. As a result, only a subset of the flow information is represented in FIG. 8 compared to that shown in FIG. 7. FIG. 8 includes an origin 802. FIG. 8 also includes an x-axis 804 and a y-axis 806 that define a flow region 850 in accordance with an embodiment. The origin 802 represents the location where the x-axis 804 and the y-axis 806 meet. The origin 802 is represented by a triangular icon in FIG. 8, but the origin may be represented differently according to various embodiments. For example the origin may be represented by other shapes, such as a dot, a crosshair, an "X", a circle, a square, a star, etc. Additionally, some embodiments may not display the x-axis 804 and/or the y-axis 806. In the embodiment shown in FIG. 8, the flow region 850 is defined by the origin 802 and is the region below the x-axis 804 and to the right of the y-axis 806. It should be appreciated that the flow region 850 may be defined in a different location with respect to the origin 802 in other embodiments. For example, the flow region may be defined to be the region below the x-axis 804 and to the left of the y-axis 806; the flow region may be defined to be the region above the x-axis 804 and to the right of the y-axis 806; or the flow region may be defined to be the region above the x-axis and to the left of the y-axis 806 according to various embodiments. According to an exemplary embodiment, the clinician may be able to select the position of the flow region with respect to the origin 802. For example, the clinician may be able to toggle through the four options described with respect to the origin and/or select one of the four options described hereinabove with respect to the origin based on inputs made through the user interface 115. FIG. 8 represents an exemplary embodiment where the selected angular range is 270 degrees to 30 degrees.

In FIG. 8, flow information from all of the fourth region 656 is represented in the flow-mode image 800. All of the fourth region 656 is within the flow region 850 and the flow information in the fourth region 656 is moving in a direction within the selected angular range (i.e., the flow information in the fourth region 656 is moving in a direction of 330 degrees, which is within the selected angular range of 270 degrees to 90 degrees). Additionally, flow information from a portion of the fifth region 658 within the flow region 850 is represented in the flow-mode image 800 since the flow information within the fifth region 658 is also moving in a direction within the selected angular range. Flow information from the portion of the fifth region 658 that is outside the flow region 850 is not represented on the flow-mode image 800 since it is outside of the selected flow region 850. The flow information from the third region 654 is not represented in the flow-mode image 800 since the flow information in the third region 654 is outside of the selected angular range (i.e., the flow information direction of the third region 654 is 170 degrees, which is not within the selected angular range of 270 degrees to 30 degrees).

According to an embodiment, the clinician may use a multi-function controller, such as the multi-function controller 300, to position an origin to designate a flow region. For example, the clinician may control the position of the origin 802 by tilting the multi-function controller 300 like a joystick. That is, the clinician may use the joystick functionality of the multi-function controller 300 to position the origin 802 with respect to the initial ultrasound image 600 or the image that is currently displayed on the display device 118. In order to obtain the exemplary flow-mode image shown in FIG. 8, the user may have used the multi-function controller 300 to position the origin 802 at the location shown in FIG. 8 during step 508 of the method 500. It should be appreciated that the origin may be positioned at any arbitrary position with respect to the currently displayed ultrasound image, depending upon the anatomy that the clinician would like to evaluate.

Figure 9:
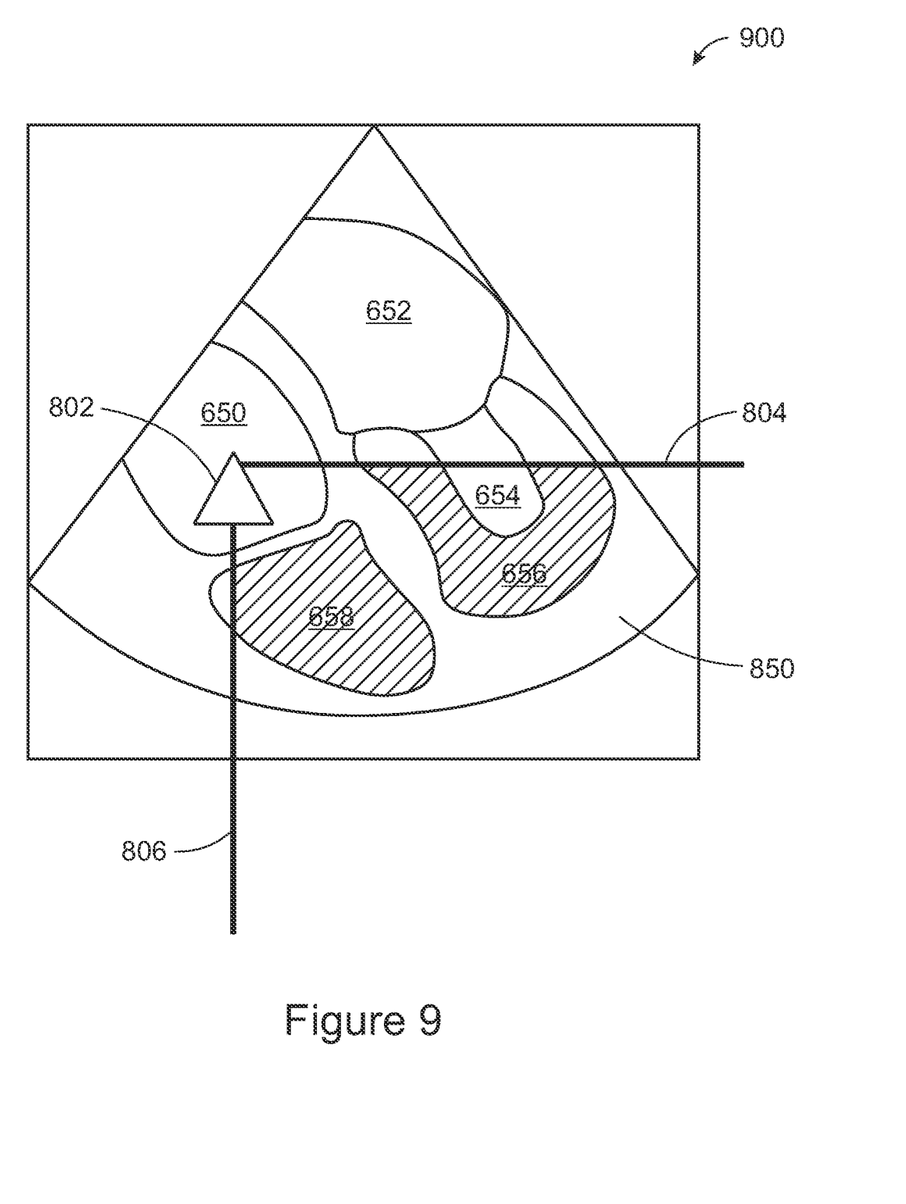
FIG. 9 is a representation of a flow-mode image in accordance with an embodiment.

FIG. 9 is representative of a flow-mode image 900 in accordance with an embodiment. The flow-mode image 900 is generated using the same underlying flow information as that shown in FIGS. 6, 7, and 8 in accordance with an embodiment. The flow region 850 in flow-mode image 900 is different than the flow region 850 in flow-mode image 800 as indicated by the different locations of the origin 802 in FIGS. 800 and 900. According to an exemplary embodiment, the user may have used the user interface 115, such as, for example, the multi-function controller 300, to move the origin 802 from the position depicted in FIG. 8 to the position depicted in FIG. 9. As discussed hereinabove, the position of the origin 802 may be selected using user interface controls other than the multi-function controller 300. For example, the clinician may use one or more input devices such as a keyboard, hard keys, a touch pad, a touch panel of a touchscreen, a track ball, rotary controls, sliders, soft keys, or any other user input devices to control the position of the flow region 850.

As discussed previously, the flow information displayed in flow region 850 is only the flow information within the angular range selected at step 510. According to the exemplary embodiment shown in FIG. 8, the angular range is from 270 degrees to 30 degrees. This means that all the flow information that is moving in a direction between 270 degree and 30 degrees is represented on the flow-mode image. As discussed previously, the flow information in the fourth region 656 and the fifth region 658 is 330 degrees. As such, the flow information in the fourth region 656 and the fifth region 658 is within the angular range that was selected for FIG. 9. Flow information that is outside of this range— i.e., the flow information that is moving in a direction that is greater than 30 degrees but less than 270 degrees—is not represented in the flow-mode image. The flow information in the third region 654 is 170 degrees. As such, the flow information in the third region 654 is outside of the selected angular range of 270 degrees to 30 degrees. Therefore, in FIG. 9, flow information from the portion of the fourth region 656 within the flow region 850 and the portion of the fifth region 658 within the flow region 850 are represented on the flow-mode image 900. However, the portion of the third region 654 within the flow region 850 is not represented on the flow-mode image 800 since the flow information in the third region 656 is outside of the selected angular range. It should be appreciated by those skilled in that art that the angular range of 270 degrees to 30 degrees is an exemplary angular range and that other angular ranges may be used. Additionally, as was described hereinabove, the user may adjust the selected angular range as multiple iterations of steps 508, 510, 512, 514, 516, and 518 are being performed. As such, the clinician can fine-tune the angular range to show exactly the desired angular range in the flow-mode image or vary the angular range to see how much flow is within the flow region within different specified angular ranges.

Figure 10:
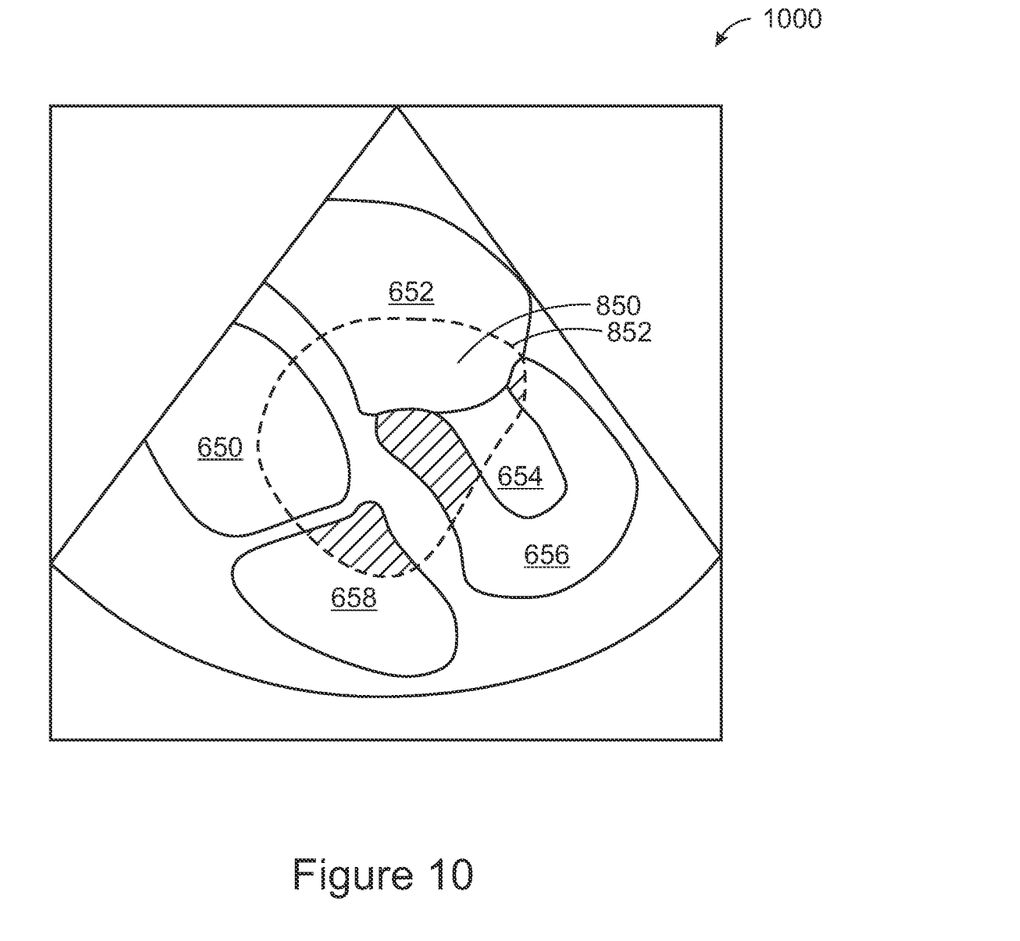
FIG. 10 is a representation of a flow-mode image in accordance with an embodiment.

FIG. 10 is a representation of a flow-mode image 1000 in accordance with an embodiment. The flow-mode image 1000 is generated using the same underlying flow information as that shown in FIGS. 6, 7, 8, and 9 in accordance with an embodiment. However, FIG. 10 is generated after the selection of a flow region 850 and the selection of an angular range. In FIG. 10, the flow region 850 is of an arbitrary shape. The clinician may have used the user interface 115 to designate a boundary 852 of the flow region 850. The angular range for the flow-mode image 1000 is between 270 degrees and 30 degrees, which is the same as the flow region used in FIGS. 8 and 9. However, the size and shape of the flow region 850 in the flow-mode image 1000, the flow information represented in the flow-mode image 1000 is different than that represented in the flow-mode image 800 or the flow-mode image 900.

Figure 11:
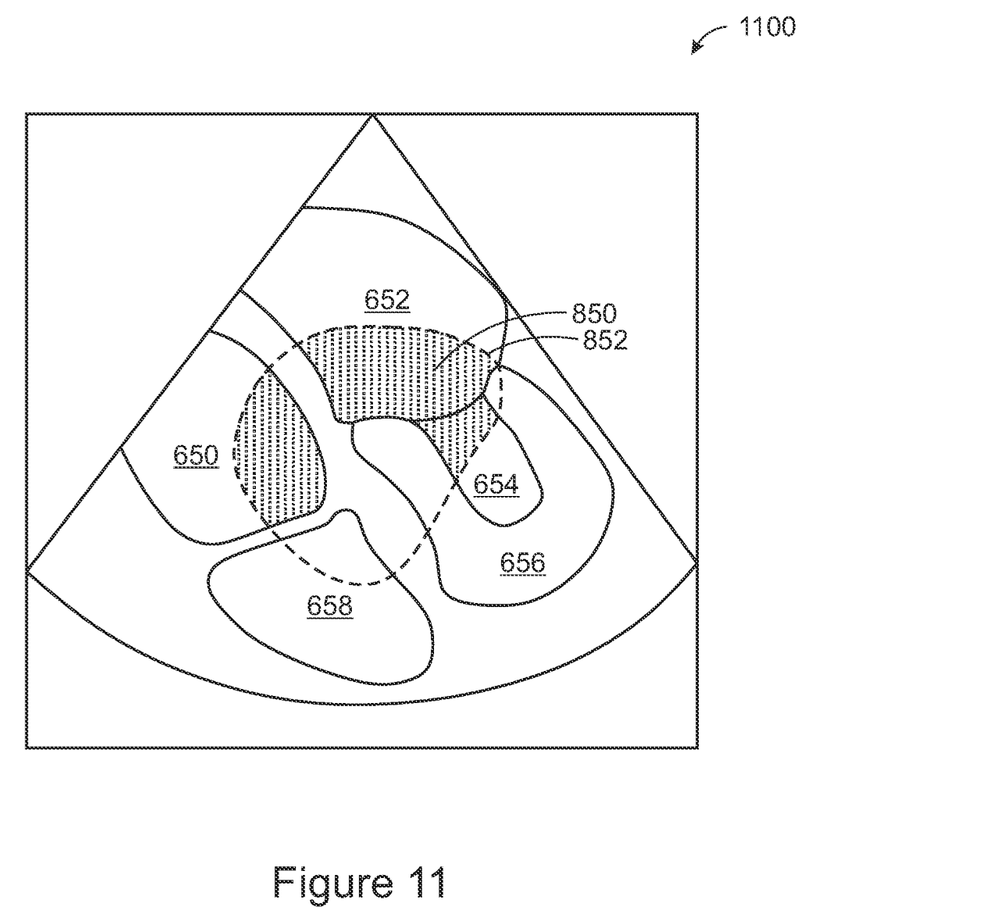
FIG. 11 is a representation of a flow-mode image in accordance with an embodiment.

FIG. 11 is a flow-mode image 1100 in accordance with an embodiment. The flow-mode image 1100 includes the flow region 850. The flow-mode image 1100 is generated using the same underlying flow information as that shown in FIGS. 6, 7, 8, 9, 10, and 11. The flow region 850 is the same size and shape as the flow region 850 in flow-mode image 1000. However, in the flow-mode image 1100, the angular range is from 90 degrees to 270 degrees. As such, the flow information represented in the flow-mode image 1100 is different than the flow information represented in the flow-mode image 1000 even though the flow region 850 is the same in both flow-mode image 1000 and flow-mode image 1100.

FIGS. 8, 9, 10, and 11 show some exemplary ways that the flow region 850 could be graphically indicated. For example, in FIGS. 8 and 9, the origin 802, the x-axis 804 and the y-axis 806 define the flow region 850. According to another embodiment, FIGS. 10 and 11 each include a boundary 852 graphically indicating the flow region 850. The boundary 852 is a dashed line, but in other embodiments, the boundary may be represented by a solid line, a dotted line, a dot-dash line, or any other type of line. It should be appreciated that the flow region could be graphically indicated in other ways according to various embodiments. Additionally, FIGS. 8, 9, 10, and 11 include examples of flow mode images that may be displayed at step 516 during the method 500 according to various embodiments.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A method of ultrasound imaging comprising:
   displaying an initial ultrasound image;
   receiving, through a user interface, a selection of a flow region, wherein the flow region includes a subset of the initial ultrasound image;
   receiving, through the user interface, a selection of an angular range, wherein the angular range determines a directional range of flow information displayed in the flow region, and wherein the angular range is less than 360 degrees; and
   displaying a flow-mode image on a display device after receiving both the selection of the flow region and the selection of the angular range, wherein the flow-mode image represents flow information that is both within the flow region and within the selected angular range, and wherein the flow-mode image does not represent flow information that is either outside the flow region or outside of the angular range,
   wherein the selection of the angular range comprises a selection of a first angle which defines a beginning of the angular range and a selection of a second angle which defines an ending of the angular range.

2. The method of claim 1, wherein the user interface comprises at least one of a multi-function controller, a trackball, a touchpad, a mouse, a touch panel of a touchscreen, or a rotary controller.

3. The method of claim 2, wherein the user interface comprises a multi-function controller that is configured to rotate, and wherein said receiving the selection of the angular range comprises receiving a rotational input through the multi-function controller to establish the angular range.

4. The method of claim 3, wherein said receiving the selection of the flow region comprises receiving a position of an origin through the multi-function controller, wherein the origin defines the flow region.

5. The method of claim 4, wherein the multi-function controller is configured to function as a joystick, and wherein said receiving the selection of the flow region comprises receiving one or more joystick inputs through the multi-function controller to position the origin.

6. The method of claim 2, wherein the user interface comprises at least one of a touch panel of a touchscreen or a touchpad, and wherein said receiving the selection of the flow region comprises receiving a gesture through the at least one of the touch panel of the touchscreen or the touchpad.

7. The method of claim 6, wherein the gesture defines an outline of the flow region.

8. The method of claim 6, wherein said receiving the selection of the angular range comprises receiving a second gesture through the at least one of the touch panel of the touchscreen or the touchpad.

9. The method of claim 1, further comprising graphically indicating the flow region after said receiving the selection of the flow region.

10. An ultrasound imaging system comprising:
    a user interface;
    an ultrasound probe;
    a display device; and
    a processor, wherein the processor is configured to:
        display an initial ultrasound image on the display device;
        receive a selection of a flow region via the user interface, wherein the flow region includes a subset of the initial ultrasound image;
        receive a selection of an angular range via the user interface, wherein the angular range determines a directional range of flow information displayed in the flow region, and wherein the angular range is less than 360 degrees;
        display a flow-mode image on the display device, wherein the flow-mode image represents flow information that is both within the flow region and within the selected angular range, and wherein the flow-mode image does not represent flow information that is either outside the flow region or outside of the angular range,
    wherein the selection of the angular range comprises a selection of a first angle which defines a beginning of the angular range and a selection of a second angle which defines an ending of the angular range.

11. The ultrasound imaging system of claim 10, wherein the user interface comprises at least one of a multi-function controller, a trackball, a touchpad, a mouse, a touch panel of a touchscreen, or a rotary controller.

12. The ultrasound imaging system of claim 10, wherein the user interface comprises a multi-function controller that is configured to rotate, and wherein the processor is configured to receive the selection of the angular range based on a command input through the multi-function controller.

13. The ultrasound imaging system of claim 10, wherein the multi-function controller is also configured to be used like a joystick.

14. The ultrasound imaging system of claim 10, wherein the user interface comprises at least one of a touch panel of a touchscreen or a touchpad, and wherein the processor is configured to receive the selection of the angular range based on a command input through the at least one of the touch panel of the touchscreen or the touchpad.

15. The ultrasound imaging system of claim 14, wherein the at least one of the touch panel of the touchscreen or the touchpad is configured to receive a first gesture to identify the flow region.

16. The ultrasound imaging system of claim 15, wherein the at least one of the touch panel of the touchscreen or a touchpad is configured to receive a second gesture to identify the angular range.

17. The ultrasound imaging system of claim 14, wherein the at least one of the touch panel of the touchscreen or the touchpad is configured to receive a gesture to identify the flow region.

18. The ultrasound imaging system of claim 10, wherein the processor is configured to graphically indicate the flow region after said receiving the selection of the flow region.

* * * * *